(12) United States Patent
Sebti

(10) Patent No.: US 7,713,960 B2
(45) Date of Patent: May 11, 2010

(54) INHIBITION OF THE RAF/MEK/P-ERK PATHWAY FOR TREATING CANCER

(75) Inventor: Said M. Sebti, Tampa, FL (US)

(73) Assignee: University of South Florida, Tampa, FL (US)

(*) Notice: Subject to any disclaimer, the term of this patent is extended or adjusted under 35 U.S.C. 154(b) by 0 days.

(21) Appl. No.: 11/490,777

(22) Filed: Jul. 21, 2006

(65) Prior Publication Data

US 2007/0021512 A1    Jan. 25, 2007

Related U.S. Application Data

(60) Provisional application No. 60/595,639, filed on Jul. 22, 2005.

(51) Int. Cl.
*A01N 43/40* (2006.01)
*A61K 31/435* (2006.01)
(52) U.S. Cl. ..................................................... 514/217
(58) Field of Classification Search ....................... None
See application file for complete search history.

(56) References Cited

U.S. PATENT DOCUMENTS

| | | | |
|---|---|---|---|
| 5,573,908 A | 11/1996 | Allen et al. | |
| 2002/0160979 A1 | 10/2002 | Banerjee et al. | |
| 2003/0068616 A1 | 4/2003 | Polansky | |
| 2003/0215528 A1 | 11/2003 | Graham et al. | |
| 2004/0106141 A1 | 6/2004 | Mischel et al. | |
| 2005/0086707 A1 | 4/2005 | Jakobovits et al. | |
| 2008/0234244 A1* | 9/2008 | Xie et al. ................... | 514/180 |

FOREIGN PATENT DOCUMENTS

WO    WO-2007/013997 A2    2/2007

OTHER PUBLICATIONS

Iishi et. al., Cancer Letters (1998), 122: 61-65.*
Park et. al., Cancer Research, 1995, 55:3504-3508.*
Iishi et. al., Cancer Letters, 1998, 122:61-65.*
Alvarez, J. et al. (2004)."Genome-Wide Analysis of STAT Target Genes—Elucidating the Mechanism of STAT-Mediated Oncogenesis," *Cancer Biol Ther* 3(11):1045-1050.
Ballif, B. et al. (2001). "Molecular Mechanisms Mediating Mammalian Mitogen-activated Protein Kinase (MAPK) Kinase (MEK)-MAPK Cell Survival Signals," *Cell Growth Differ* 12:397-408.
Biernacki, W. et al. (1989) "The effect of Six Months of Daily Treatment With the Beta-w Agonist Oral Ipirbuterol on Pulmonary Hemydynamics in Patients With Chronic Hypoxic cor Pulmonale Receiving Long-Term Oxygen Therapy," *Am Rev Respir Dis.* 139(2):492-497.
Blaskovich, M. et al. (2003). "Discovery of JSI-124 (Cucurbitacin I), a Selective Janus Kinase/Signal Transducer and Activator of Transcription 3 Signaling Pathway Inhibitor with Potent Antitumor Activity against Human and Murine Cancer Cells in Mice," *Cancer Res* 63:1270-1279.

Borg, A. et al. (1990). "HER-2/neu Amplification Predicts Poor Survival in Node-Positive Breast Cancer," *Cancer Res* 50:4332-4337.
Bos, J. (1989). "*Ras* oncogenes in human cancer: a review," *Cancer Res* 49:4682-4689.
Budillon, A. et al. (1999) "8-CI-cAMP Antagonizes Mitogen-Activated Protein Kinase Activation And Cell Growth Stimulation Induced by Epidermal Growth Factor," *Br J Cancer* 81(7):1134-1141.
Cakir, Y. et al. (2002) "Beta-Adrenergic and Arachidonic Acid-Mediated Growth Regulation of Human Breast Cancer Cell Lines," *Intl J Onc* 21:153-157.
Carman, C. et al. (1998) "G-protein-Coupled Receptors: Turn-Ons and Turn-Offs," *Curr Opin Neurobiol* 8:335-344.
Cox, M. et al. (2000)."Activated 3',5'-Cyclic AMP-Dependent Protein Kinase Is Sufficient to Induce Neuroendocrine-like Differentiation of the LNCaP Prostate Tumor Cell Line," *J Biol Chem* 275(118):13812-13818.
Dhillon, A. et al. (2002) "Untying the Regulation of the Rat-1 Kinase," *Arch Biochem Biophys* 404:3-9.
Di Marco, E. et al. (1989). "Autocrine Interaction Between TGFα and the EGF-Receptor: Quantitative Requirements for Induction of the Malignant Phenotype," *Oncogene* 4:831-838.
Dumaz, N. et al. (2005)"Integrating signals between cAMP and the RAS/RAF/MEK/ERK signalling pathways," *Febs J* 272:3491-3504.
English, J. et al. (2002). "Pharmacological Inhibitors of MAPK Pathways," *Trends Pharmacol Sci* 23(1):40-45.
Enserink, J. et al. (2002) "A Novel Epac-Specific cAMP Analogue Demonstrates Independent Regulation of Rap1 and ERK," *Nat Cell Biol* 4:901-906.
Erhardt, P. et al. (1995). "Differential Regulation of Raf-1 and B-Raf and Ras-Dependent Activation of Mitogen-Activated Protein Kinase by Cyclic AMP in PC12 Cells," *Mol Cell Biol* 15(10):5524-5530.
Fleming, T. et al. (1992)."Platelet-Derived Growth Factor (PDGF) Receptor Activation in Cell Transformation and Human Malignancy," *Exp Gerontol* 27:523-532.
Force, T. et al. (2004) "Inhibitors of Protein Kinase Signaling Pathways: Emerging Therapies for Cardiovascular Disease," *Circulation* 109:1196-1205.
Fresno Vara, J. et al. (2004)."P13K/Akt Signalling Pathway and Cancer," *Cancer Treat Rev* 30:193-204.
Graells, J. et al. (2004). "Overproduction of VEGF165 Concomitantly Expressed with its Receptors Promotes Growth and Survival of Melanoma Cells through MAPK and PI3K Signaling," *J Invest Dermatol* 123:1151-1161.
Grassi, V. et al. (1986). Oral Beta2-selective adrenergic bronchodilators, *Int J Clin Pharmacol Res* 6:93-103.

(Continued)

*Primary Examiner*—Frederick Krass
*Assistant Examiner*—Marcos Sznaidman
(74) *Attorney, Agent, or Firm*—Morrison & Foerster LLP

(57) ABSTRACT

The invention disclosed herein provides for methods of treating cancer using inhibitors of the Raf/Mek/P-Erk 1/2 pathway. These inhibitors include B2AR agonists (such as ARA-211 (pirbuterol) and isoproterenol), adenylyl cyclase activators, cAMP analogs and Epac activators. The invention also provides methods for diagnosing cancer in an individual.

5 Claims, 7 Drawing Sheets

OTHER PUBLICATIONS

Graves, L. et al. (1993). "Protein Kinase A Antagonizes Platelet-Derived Growth Factor-Induced Signaling by Mitogen-Activated Protein Kinase in Human Arterial Smooth Muscle Cells," *Proc Natl Acad Sci U S A* 90:10300-10304.

Hafner, S. et al. (1994). "Mechanism of Inhibition of Raf-1 by Protein Kinase A," *Mol Cell Biol* 14:6696-6703.

Hagemann, C. et al. (2001). "The Ups and Downs of MEK Kinase Interactions," *Cell Signal* 13:863-875.

Hamdad, N. et al. (1996) "β2-Adrenergic Dilation of Conductance Coronary Arteries Involves Flow-Dependent NO Formation in Conscious Dogs," *Am J Physiol Soc.* pp. H1926-H1937.

Hanahan, D. et al. (2000). "The Hallmarks of Cancer," *Cell* 100:57-70.

Hao, D. et al. (2002). "Inhibiting Signal Transduction: Recent Advances in the Development of Receptor Tyrosine Kinase and Ras Inhibitors," *Cancer Invest* 20(3):387-404.

Jiang, Z. et al. (2004). "Alpha-Methylacyl-Coa Racemase: A Multi-Institutional Study of a New Prostate Cancer Marker," *Histopathology* 45:218-225.

Jin, W. et al. (2003). "Roles of the PI-3K and MEK Pathways in Ras-Mediated Chemoresistance in Breast Cancer Cells," *Br J Cancer* 89:185-191.

Johnson, G. et al. (2002). "Mitogen-Activated Protein Kinase Pathways Mediated by ERK, JNK, and p38 Protein Kinases," *Science* 298:1911-1912.

Johnson, J. et al. (2005). "Approval Summary for Erlotinib for Treatment of Patients with Locally Advanced or Metastatic Non Small Cell Lung Cancer after Failure of at Least One Prior Chemotherapy Regimen," *Clin Cancer Res* 11(18):6414-6421.

Khosravi-Far, R. et al. (1996). "Oncogenic Ras Activation of Raf/Mitogen-Activated Protein Kinase-Independent Pathways Is Sufficient to Cause Tumorigenic Transformation," *Mol Cell Biol* 16(7):3923-3933.

Kyriakis, J. et al. (1992) "Raf-1 Activates MAP Kinase-Kinase," *Nature* 358:417-421.

Lavoie, C. et al. (2002) "1/ 2-Adrenergic Receptor Heterodimerization Regulates 2-Adrenergic Receptor Internalization and ERK Signaling Efficacy," *J Biol Chem* 277(38):35402-35410.

Lerner, E. et al. (1997). "Inhibition of the Prenylation of K-Ras, But Not H- or N-Ras, is Highly Resistant to CAAX Peptidomimetics and Requires Both A Farnesyltransferase and A Geranylgeranyltransferase I Inhibitor in Human Tumor Cell Lines," *Oncogene* 15:1283-1288.

Maudsley, S. et al. (2000). "The b2-Adrenergic Receptor Mediates Extracellular Signal-regulated Kinase Activation via Assembly of a Multi-receptor Complex with the Epidermal Growth Factor Receptor," *J Biol Chem* 275(13):9572-9580.

Ming, Z. et al. (1997) "β2-Adrenergic Dilation of Resistance Coronary Vessels Involves KATP Channels and Nitric Oxide in Conscious Dogs," *Circulation* 95:1568-1576.

Moore, P. et al. (1978). "Pirbuterol, a Selective Beta2 Adrenergic Bronchodilator," *J Pharmacol Exp Ther* 207(2):410-418.

Parent, R. et al. (1993) "Nitric Oxide Formation Contributes to Beta-Adrenergic Dilation of Resistance Coronary Vessels in Conscious Dogs," *Circ Res.* 73(2):241-251.

Plummer, H. et al (2005) "Expression of G-protein Inwardly Rectifying Potassium Channels (Girks) in Lung Cancer Cell Lines," *BMC Cancer* 5:104-114.

Ratain, M. et al. (2004) "Preliminary Antitumor Activity of BAY 43-9006 in Metastatic Renal Cell Carcinoma and Other Advanced Refractory Solid Tumors in a Phase II Randomized Discontinuation Trial (RDT)," ASCO Presentation, 2004 *ASCO Annual Meeting Proceedings (Post-Meeting Edition) Journal of Clin. Oncology* 22(14S):Abstract. No. 4501, 23 pages.

Redell, M. et al. (2005). "Targeting Transcription Factors for Cancer Therapy," *Curr Pharm Des* 11:2873-2887.

Schmitt, J. et al. (2001). "Cyclic AMP-Mediated Inhibition of Cell Growth Requires the Small G Protein Rap1," *Mol Cell Biol* 21(11):3671-3683.

Schmitt, J. et al. (2002). "PKA Phosphorylation of Src Mediates cAMP's Inhibition of Cell Growth via Rap1," *Mol Cell* 9:85-94.

Sebolt-Leopold, J. (2000). "Development of Anticancer Drugs Targeting the MAP Kinase Pathway," *Oncogene* 19:6594-6599.

Sebolt-Leopold, J. et al. (1999). "Blockade of the MAP Kinase Pathway Suppresses Growth of Colon Tumors in Vivo," *Nat Med* 5:810-816.

Sevetson, B. et al. (1993). "Increasing cAMP Attenuates Activation of Mitogen-Activated Protein Kinase," *Proc Natl Acad Sci USA* 90:10305-10309.

Slamon, D. et al. (1987). "Human Breast Cancer: Correlation of Relapse and Survival with Amplification of the HER-2/neu Oncogene," *Science* 235:177-182.

Slotkin, T. et al. (2000). "Antimitotic and Cytotoxic Effects of Theophylline in MDA-MB-231 Human Breast Cancer Cells," *Breast Cancer Research and Treatment* 64:259-267.

Slotkin, T. et al. (2000). "B-Adrenoceptor Signaling and Its Control of Cell Replication in MDA-MB-231 Human Breast Cancer Cells," *Breast Cancer Research and Treatment* 60:153-166.

Sood, A. et al (2006) "Stress Hormone-Mediated Invation of Ovarian Cancer Cells," *Clin Cancer Res* 12(2) 369-375.

Steen, S. et al. (1974). "Pyrbuterol: A New Bronchodilator. Phase I—Single Dose Study," *Curr Ther Res Clin Exp* 16:1077-1081.

Steinberg, S. (2000). "The Cellular Actions of b-Adrenergic Receptor Agonists Looking Beyond Camp," *Circ Res* 87:1079-1082.

Stork, P. et al. (2002) "Crosstalk between cAMP and MAP Kinase Signaling in the Regulation of Cell Proliferation," *Trends Cell Biol* 12:258-266.

Strobl, J. et al. (1995) "Mitogenic Signal Transduction in Human Breast Cancer Cells," *Gen Pharmacol* 26:1643-1649.

Sun, J. et al. (2003). "Geranylgeranyltransferase I Inhibitor GGTI-2154 Induces Breast Carcinoma Apoptosis and Tumor Regression in H-Ras Transgenic Mice," *Cancer Res* 63:8922-8929.

Sun, J. et al. (2005). "Inhibiting angiogenesis and Tumorigenesis by a Synthetic Molecule That Blocks Binding of Both VEGF and PDGF to Their Receptors," *Oncogene* 24:4701-4709.

Tortora, G. et al. (2002). "Protein Kinase A as Target for Novel Integrated Strategies of Cancer Therapy," *Ann N Y Acad Sci* 968:139-147.

Troadec, J. et al. (2002). "Activation of the Mitogen-Activated Protein Kinase (ERK1/2) Signaling Pathway by Cyclic AMP Potentiates the Neuroprotective Effect of the Neurotransmitter Noradrenaline on Dopaminergic Neurons," *Mol Pharmacol* 62:1043-1052.

Veber, N. et al. (1994). "Evidence for a Growth Effect of Epidermal Growth Factor on MDA-MB-231 Breast Cancer Cells," *European Journal of Cancer* 30A(9):1352-1359.

Vossler, M. et al. (1997). "cAMP Activates MAP Kinase and Elk-1 through a B-Raf- and Rap1-Dependent Pathway," *Cell* 89:73-82.

Watanabe, M. et al. (1996). "An Effect of K-ras Gene Mutation on Epidermal Growth Factor Receptor Signal Transduction in PANC-1 Pancreatic Carcinoma Cells," *Int. J. Cancer* 67:264-268.

Weinstein-Oppenheimer, C. et al. (2000). "The Raf Signal Transduction Cascade as a Target for Chemotherapeutic Intervention in Growth Factor-Responsive Tumors," *Pharmacology & Therapeutics* 88:229-279.

Weldon, C. et al. (2002). "Identification of Mitogen-Activated Protein Kinase Kinase as a Chemoresistant Pathway in MCF-7 Cells by Using Gene Expression Microarray," *Surgery* 132(2):293-301.

Wu, J. et al. (1993). "Inhibition of the EGF-Activated MAP Kinase Signaling Pathway by Adenosine 3 Prime, 5 Prime-Monophosphate," *Science* 262:1065-1069.

Yeh, T. et al. (2005). "Validation and Use of a Biomarker for Development of the MEK 1/2 Inhibitor ARRAY-142886 (AZD6244)," *Array Biopharma* 2 pages.

Yu, C-L. (1995). "Enhanced DNA-Binding Activity of a Stat3-Related Protein in Cells Transformed by the Src Oncoprotein," *Science* 269:81-83.

Yu, M. et al. (1998). "Elevated Cyclic AMP Suppresses ConA-Induced MT1-MMP Expression in MDA-MB-231 Human Breast Cancer Cells," *Clin. Exp. Metastasis* 16(2):185-191.

International Search Report mailed on Jan. 17, 2008, for PCT Application No. PCT/US06/28294, filed on Jul. 21, 2006, three pages.

Tatsuta, M. et al. (1989). "Inhibition by Neostigmine and Isoproterenol and Promotion by Atropine of Experimental Carcinogenesis in Rat Stomach by N-methyl-N'-nitro-N-nitrosoguanidine," *Int. J. Cancer* 44:188-189.

Carie, A.E. et al. (2007, e-published on Jan. 29, 2007). "A Chemical Biology Approach Identifies a Beta-2 Adrenergic Receptor Agonist That Causes Human Tumor Regression by Blocking the Raf-1/Mek-1/Erk1/2 Pathway," *Oncogene* 26:3777-3778.

* cited by examiner

INHIBITION OF THE RAF/MEK/P-ERK PATHWAY FOR TREATING CANCER

CROSS-REFERENCE TO RELATED APPLICATIONS

This application claims priority to U.S. Provisional Application No. 60/595,639, filed on Jul. 22, 2005. The provisional application is incorporated by reference herein in its entirety.

STATEMENT REGARDING FEDERALLY SPONSORED RESEARCH OR DEVELOPMENT

This invention was made with government support under 5P01CA78038 awarded by the National Institutes of Health. The government has certain rights in the invention.

TECHNICAL FIELD

The invention relates to personalized medical treatments for cancer that involve targeting specific cancers by its molecular fingerprint. More specifically, the invention provides for treatment of various cancers by using inhibitors of the Raf-1/Mek-1/Erk 1/2 pathway. These inhibitors include B2AR agonists (such as ARA-211 (pirbuterol) and isoproterenol), adenylyl cyclase activators, cAMP analogs and Epac (exchange protein directly activated by cyclic AMP) activators. In addition, the invention provides for diagnosis of various cancers by analyzing biological samples for the presence of a B2AR agonist and phosphorylated extracellular-signaling regulated kinase (Erk) proteins.

BACKGROUND OF INVENTION

Throughout the specification, various references to scientific publications are indicated by the use of numbers. The full citations for these scientific publications are located after the Examples section. The disclosures of all publications, patents, patent applications and published patent applications referred to herein are hereby incorporated herein by reference in their entireties.

Malignant transformation of normal to cancer cells requires the acquisition of several oncogenic traits such as uncontrolled cell division, resistance to programmed cell death (apoptosis), invasion and angiogenesis (1). These malignant transformation traits are believed to be the consequence of the accumulation of genetic alterations that result in dysregulated signal transduction circuits (2, 3). Such genetic alterations can simply be point mutations that result in constitutive activation of key signal transducers such as Ras, a GTP/GDP binding GTPase that contributes to 30% of all human cancers (4). Alternatively, these alterations can involve entire genes such as the receptor tyrosine kinases epidermal growth factor receptor (EGFR) and ErbB2 that are found overexpressed in many major human cancers including breast and lung tumors (5, 6). Often such genetic alterations result in constitutive activation of common downstream signal transduction pathways such as the mitogen activated protein (MAP) kinase cascade c-Raf-1, Mek-1, Erk 1/2, p38 and JNK (7, 8). Other pathways involved in uncontrolled proliferation, apoptosis, invasion and angiogenesis also include those mediated by the signal transducer and activator of transcription STAT3 and the serine/threonine kinase Akt (9, 10). Not only have these oncogenic and tumor survival pathways been found constitutively activated in the great majority of human cancers but also their hyperactivation has been associated with poor prognosis and resistance to chemotherapy in cancer patients (11, 12). This has prompted drug discovery efforts targeting receptor tyrosine kinases, for example, Ras, c-Raf-1, Mek, Akt and STAT3, to thwart aberrant signal transduction pathways in tumor cells (13-16).

In normal cells, it is well established that the activation of the kinase Erk 1/2 is regulated by receptor tyrosine kinases such as EGFR and platelet-derived growth factor receptor (PDGFR) via activation of Ras, which in turn activates the Raf-1/Mek-1/Erk 1/2 cascade (17). Because this signal transduction pathway is hyperactivated in many human cancers, inhibitors of receptor tyrosine kinases, Ras, c-Raf-1 and Mek-1 have all been identified and are at various stages of development (18, 19). One of these inhibitors, gefitinib (marketed as Iressa), an EGFR kinase inhibitor, was recently approved by the FDA for the treatment of patients with lung cancer.

More recently, the beta-2-adrenergic receptor (B2AR) stimulation of cyclic AMP (cAMP) has been shown to regulate the activation of Erk 1/2 in normal cells (20, 21). Interestingly, in some normal cells such as cardiac myocytes and bone cells, B2AR stimulation was shown to activate Erk 1/2, whereas in others such as adipocytes and endothelial cells it was shown to inhibit Erk 1/2 activation (21). In tumor cells, however, whether B2AR stimulation results in inhibition of the Raf/Mek/Erk kinase cascade is not known. The present invention provides for methods of treating cancer by inhibiting the Raf/Mek/Erk kinase cascade.

BRIEF SUMMARY OF THE INVENTION

The invention provides for a method of treating cancer in an individual in need thereof by administering to the individual an effective amount of an inhibitor of the Raf-1/Mek-1/P-Erk 1/2 pathway. In one aspect, the inhibitors are selected from the group consisting of a B2AR agonist, an adenylyl cyclase activator, a cAMP analog and an Epac activator.

The invention also provides a method of cancer therapy involving the stimulation of the B2AR which causes human tumor regression by blocking the Raf-1/Mek-1/Erk 1/2 pathway. Thus, in one aspect, the invention provides for a method for suppressing tumor growth in an individual in need thereof by administering to the individual an amount of a B2AR agonist that is effective for suppressing tumor growth.

In another aspect, the invention provides for a method for treating cancer in an individual in need thereof by administering to the individual an effective amount of a B2AR agonist.

In another aspect, the invention provides for a method for suppressing tumor growth in an individual in need thereof comprising administering to the individual an amount of a B2AR agonist that can block the Raf-1 signal transduction pathway.

In another aspect, the invention provides for a method for suppressing tumor growth in an individual in need thereof by administering to the individual an amount of a B2AR agonist that can block the Mek-1 signal transduction pathway.

In another aspect, the invention provides for a method for suppressing tumor growth in an individual in need thereof by administering to the individual an effective amount of a B2AR agonist that can activate Epac and Rap1, thereby suppressing tumor growth.

In another aspect, the invention provides for a method of treating cancer in an individual in need thereof by administering to the individual an effective amount of a B2AR agonist that inhibits the phosphorylation of Erk 1/2 protein In another aspect, the invention provides for a method of delaying the development of cancer in an individual by administering to the individual an amount of a B2AR agonist that is effective for stimulating a B2AR.

In another aspect, the invention provides for a method of treating cancer in an individual in need thereof by administering an effective amount of a B2AR agonist that results in the elevation of cAMP levels and the inhibition of the phosphorylation of Erk protein.

In another aspect, the invention provides for a method of diagnosing an individual with cancer by: (a) obtaining a biological sample from the individual; (b) determining whether a B2AR for an agonist is present in the biological sample; (c) determining if the Erk protein is phosphorylated in the cells contained within the biological sample wherein the presence of a B2AR for an agonist and a phosphorylated Erk protein is indicative of cancer.

DETAILED DESCRIPTION OF THE INVENTION

Figure 1:
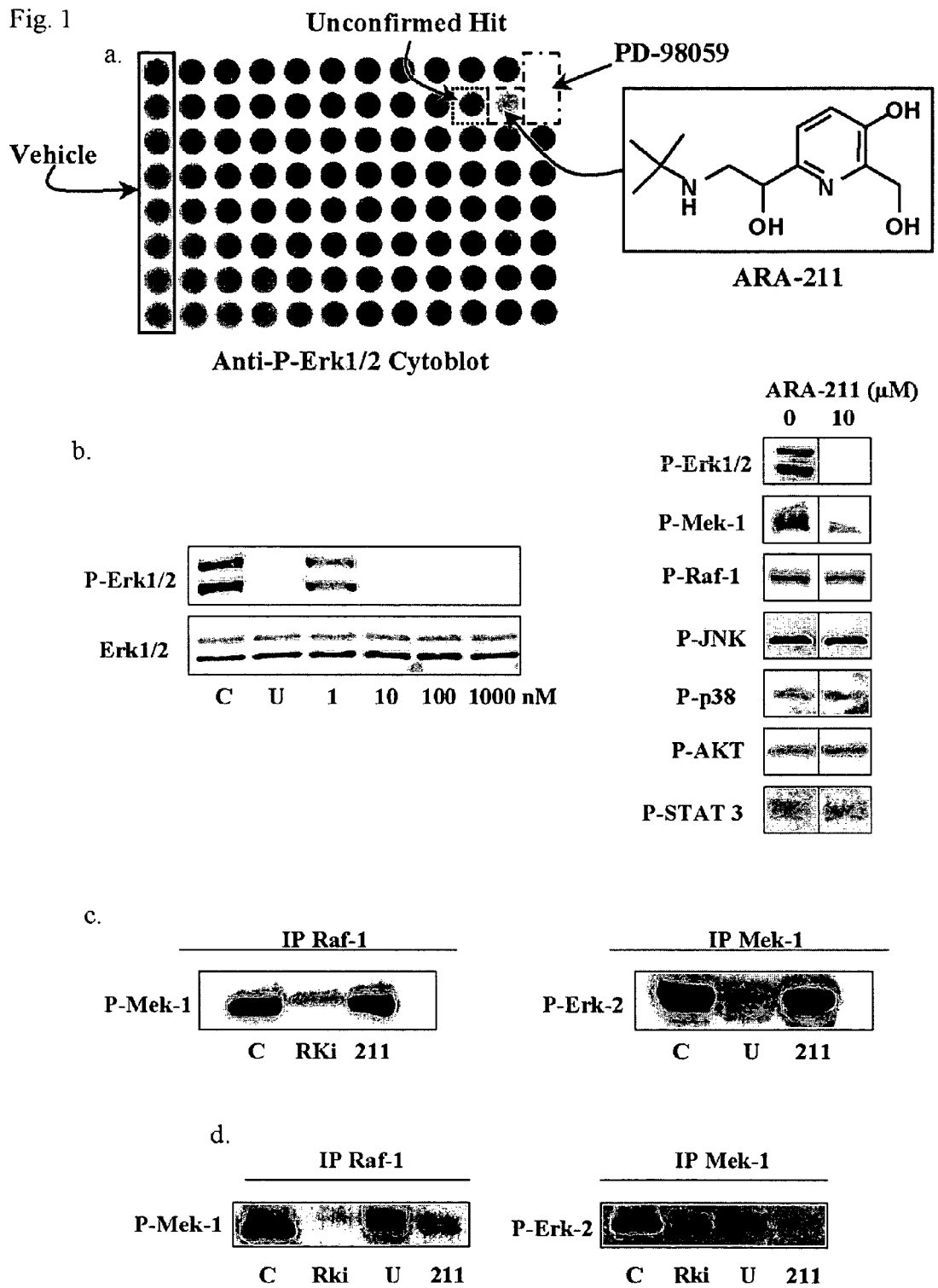
FIG. 1 depicts the identification of ARA-211 as a suppressor of P-Erk 1/2 (phosphorylated-Erk 1/2) levels in MDA-MB-231 breast cancer cells and the structure of ARA-211 itself. (a) High throughput screening identified ARA-211. MDA-MB-231 cells were plated in twenty-five 96-well plates, treated with vehicle (8 wells), PD-98059 (2 wells) or 2000 compounds (1 compound/well) from the NCI diversity set, and the plates processed for immunocytoblotting with an anti-phospho-Erk 1/2 antibody as described under Materials and Methods infra. Plate #23 is shown treated with vehicle (vertical box on left side with solid black line), PD-98059 (upper corner of the rightmost column with dashed lines), unconfirmed hit (second dot from the top in the third column from the right with dashed lines) and ARA-211 (second dot from the top in the second column from the right with dashed lines). (b) ARA-211 treatment of MDA-MB-231 cells and Western blotting were performed as described under Materials and Methods and resulted in suppression of P-Erk 1/2 and P-Mek1 but not P-Raf, P-JNK, P-p38, P-Akt and P-STAT3. (c) ARA-211 does not inhibit Raf-1 and Mek-1 kinases in vitro. Raf-1 and Mek-1 were immunoprecipitated from MDA-MB-231 cells and treated in vitro with ARA-211, Rki or PD-98059 and kinase assays followed by SDS-PAGE were performed as described in Materials and Methods. (d) ARA-211 inhibits Raf-1 and Mek-1 kinases when intact cells are treated. Similar experiments were performed as in (c) except that the intact cells were first treated with the compounds prior to immunoprecipitation and kinase assays. All experiments in b, c and d are representative of at least 3 independent experiments.

The present invention provides for methods of treating cancer in an individual in need thereof by administering to the individual an effective amount of an inhibitor of the Raf-1/Mek-1/P-Erk 1/2 pathway. Non-limiting examples of inhibitors that can be used to inhibit the Raf-1/Mek-1/P-Erk 1/2 pathway include beta-2-adrenergic receptor (B2AR) agonists, adenylyl cyclase activators, cAMP analogs and Epac activators. In one embodiment, the invention provides for methods of suppressing tumor growth and/or tumor regression by using a B2AR agonist. Without being bound by theory, the use of B2AR agonist leads to inactivation of a signal transduction pathway that includes Raf-1, Mek-1, and Erk 1/2.

The Role of beta-2-adrenergic Receptor in Signal Transduction Pathways

The mitogen activated protein kinases c-Raf-1, Mek-1 and Erk 1/2 are found to be aberrantly activated in many human cancers. By using a chemical biology approach, the inventor has demonstrated that the stimulation of the B2AR causes tumor regression. This biological effect may occur by blocking the c-Raf-1/Mek-1/Erk 1/2 pathway. Using a cytoblot specific for phospho-Erk 1/2 (pErk 1/2), the inventor has identified a small molecule, ARA-211, which suppresses P-Mek and P-Erk 1/2 but not P-JNK, P-p38, P-Akt and P-STAT3 levels.

An ACS chemical search coupled with in vitro and in vivo studies demonstrated that ARA-211 (also known as Pirbuterol or 2-hydroxymethyl-3-hydroxy-6-(1-hydroxy-2-tert-butylaminoethyl) pyridine, dihydrochloride) is a selective B2AR agonist which can induce cyclic AMP (cAMP) production and protein kinase A (PKA) activation. The chemical structure of ARA-211 is shown in the right hand panel of FIG. 1a. These effects, in turn, result in a blockade of Raf-1 and Mek-1 kinase activities and also inhibition of anchorage-dependent and independent tumor growth. Similar results were also obtained with another B2AR agonist, isoproterenol.

Biological Effects of ARA-211

In general, ARA-211 is effective in tumors where it can activate B2AR, increase the level of cyclic AMP (cAMP) and decrease P-Erk 1/2 levels. The increase of cAMP can have two effects: (1) activate protein kinase A (PKA) and (2) activate a guanine nucleotide exchange protein called Epac. The activation of Epac affects the Raf pathway in that it activates Rap1 which in turn prevents c-Raf-1 activation, thus preventing c-Raf-1 from activating proteins later downstream, such as Mek-1 and Erk 1/2. As such, B2AR stimulation with ARA-211 and other B2AR agonists is a novel approach to cancer therapy in human cancers where this stimulation results in suppression of the c-Raf/Mek-1/Erk 1/2 oncogenic and tumor survival pathway. The inventor has observed similar results with another B2AR, isoproterenol.

Other Inhibitors of the Raf-1/Mek-1/P-Erk 1/2 Pathway

The Raf-1/Mek-1/P-Erk 1/2 pathway can also be inhibited using other inhibitors other than B2AR agonists. One group of inhibitors that can be used is adenylyl cyclase activators. A non-limiting example of an adenylyl cyclase activator than can be used is forskolin. Other types of adenylyl cyclase activators will be well-known to those of ordinary skill in the art. In addition, cAMP analogs are another group of inhibitors that can be used to inhibit the Raf-1 /Mek-1/P-Erk 1/2 pathway. Non-limiting examples of cAMP analogs that may be used include: chlorophenylthio-cAMP (CPT-cAMP); dibutyryl-cAMP; 8-bromo-cAMP; 8-(4-chlorophenylthio)-cAMP; N6,O2'-dibutyryl-cAMP; N6,O2'-dioctanoyl-cAMP, and 2'-O-(N-methylanthraniloyl)-cAMP. Other types of cAMP analogs will be well-known to those of ordinary skill in the art.

Yet another group of inhibitors that can be used to inhibit the Raf-1/Mek-1/P-Erk 1/2 pathway are Epac activators. Non-limiting examples of Epac activators include 8-Br-cAMP; 8-bromo-2'-O-methyladenosine-3',5'-cyclic monophosphate (8-Br-2'-O-Me-cAMP); 8-(4-chlorophenylthio)-2'-O-methyladenosine-3',5'-cyclic monophosphate(8-pCPT-2'-O-Me-cAMP/8-CP-2'-O-Me-cAMP); 8-(4-chlorophenylthio)-2'-O-methyladenosine-3',5'-cyclic monophosphorothioate, Sp-isomer(Sp-8-pCPT-2'-O-Me-cAMPS/Sp-8-CPT-2'-O-Me-cAMPS); 8-(4-hydroxyphenylthio)-2'-O-methyladenosine-3',5'-cyclic monophosphate (8-pHPT-2'-O-Me-cAMP); and 8-(4-methoxyphenylthio)-2'-O-methyladenosine-3',5'-cyclic monophosphate(8-pMeOPT-2'-O-Me-cAMP). Other types of Epac activators will be well-known to those of ordinary skill in the art.

Therapeutic Uses

The invention provides for various cancer therapeutic uses for inhibitors of the Raf-1/Mek-1/P-Erk 1/2 pathway, for example, B2AR agonists, adenylyl cyclase activators, cAMP analogs, and Epac activators. In one aspect, the invention provides for a method of suppressing tumor growth in an individual in need thereof. This is accomplished by administering to the individual an effective amount of the B2AR agonist that results in the cessation or retardation or slowing of the growth of the tumor cells. As discussed infra, the cessation of tumor growth may occur via several possible ways. The first way occurs via B2AR blocking of the Raf-1 pathway. In one embodiment, ARA-211 prevents the activation of c-Raf-1. In another embodiment, ARA-211 prevents the activation of b-Raf-1. Another possible way is that ARA-211 causes the elevation of cAMP levels which in turn, activates Epac. Epac acts as a guanine nucleotide exchange protein and activates Rap1 which in turn inactivates the Raf- 1. Another possible way is that ARA-211 causes the increase of cAMP levels which activate protein kinase A, which has the downstream effect of shutting down Raf-1 and subsequently inhibiting Mek kinase and decreasing the levels of P-Erk 1/2.

Yet another therapeutic use for inhibitors of the Raf-1/Mek-1/P-Erk 1/2 pathway (e.g., B2AR agonists, adenylyl cyclase activators, cAMP analogs, and Epac activators) is for tumor regression. While the suppression of tumor growth is desirable in an individual who is afflicted with cancer, the mere suppression of growth alone still leaves a tumor in the individual. The additional action of regression would cause the tumor to become smaller in size.

In such ways, the invention provides for a method of cancer treatment for an individual in need thereof by administering an effective amount of an inhibitor of the Raf-1/Mek-1/P-Erk 1/2 pathway. In one embodiment, the B2AR is stimulated such that inhibition of P-Erk 1/2 protein is achieved. This can be done using ARA-211, isoproterenol or other B2AR agonists. As used herein, "treatment" is an approach for obtaining beneficial or desired clinical results. For purposes of this invention, beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total). The methods of the invention contemplate any one or more of these aspects of treatment.

The term "effective amount" used herein refers to an amount of an inhibitor of the Raf-1/Mek-1/P-Erk 1/2 pathway (e.g., B2AR agonists, adenylyl cyclase activators, cAMP analogs, and Epac activators) or combinations of two or more these agonists that is sufficient to treat the cancer (e.g., ameliorate, palliate, lessen, and/or delay one or more of its symptoms). In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

In some embodiments, there is provided a method of treating a primary tumor. In some embodiments, there is provided a method of treating metastatic cancer (that is, cancer that has metastasized from the primary tumor). In some embodiments, there is provided a method of treating cancer at advanced stage(s).

It is possible to administer an inhibitor of the Raf-1/Mek-1/P-Erk 1/2 pathway (e.g., B2AR agonists such as ARA-211 and isoproterenol) to delay the development of cancer. In one embodiment, the delaying of the development of cancer effectively prevents cancer from developing.

It is contemplated that all types of cancer can be treated by this invention. The cancer to be treated will have cells that can be stimulated through a B2AR such that subsequent phosphorylation of P-Erk 1/2 is inhibited.

Administration of B2AR Agonists and Other Inhibitors of the Raf-1/Mek-1/P-Erk 1/2 Pathway Methods of administration can vary depending on what type of aberrant growth is being treated. In one embodiment, oral delivery is used. In another embodiment, local treatment is used. For cutaneous conditions, a topical application would be appropriate. In one embodiment, B2AR agonists (e.g., ARA-211 or isoproterenol) are administered. Systemic administration of B2AR agonist is also contemplated, for example by intravenous, oral, inhalant, parenteral, intraperitoneal, or topical methods of delivery.

The B2AR agonists of the present invention may be administered as a composition, for example, as a pharmaceutical composition containing the compounds and a pharmaceutically acceptable carrier or diluent. The B2AR agonist can also be mixed with other active materials that do not impair the desired action. The active materials, in accordance with the present invention, may be administered by any acceptable route including, but not limited to, orally or parenterally (e.g., intravenously, intradermally, subcutaneously, intramuscularly, by an airborne delivery system, topically, etc.), in liquid or solid form.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. Suitable pharmaceutical carriers include, but are not limited to, sterile water; saline, dextrose; dextrose in water or saline.

Formulation and Dosages

The amount of ARA-211, isoproterenol, and other B2AR agonists that can be used to suppress tumor growth, to cause tumor regression, and to halt growth of cancer cells is an amount that is effective to stimulate B2AR such that it will cause blockage of the Raf-1/Mek-1/Erk signaling pathway. Likewise, the amount of other inhibitors of the Raf-1/Mek-1/Erk signaling pathway that can be used to suppress tumor growth, to cause tumor regression, and to halt growth of cancer cells should also be an amount that is effective to cause blockage of the Raf-1/Mek-1/Erk signaling pathway and lead to a slowing or cessation of cancer cell growth. This amount should not be so high as to cause toxicity or other negative health effects. Examples of dosages that can be used are found in Steen et al., *Curr. Ther. Clin. Exp.*, 16: 1077-1081 (1974); Moore et al., *J. Pharmacol. Exp. Ther.*, 207: 410-418 (1978); and Graves et al., *Int. J. Clin. Pharmacol. Res.*, 6:93-103 (1986).

Other B2AR agonists that can also be used include, but are not limited to, salbutamol, salmeterol, formoterol, and terbutaline. The amount used for these B2AR agonists (such as salbutamol, salmeterol, formoterol, and terbutaline) is an amount sufficient to stimulate the B2AR and still to avoid toxicity in humans. The dosages for these agonists have been filed with the Food and Drug Administration (FDA). As such, the amount of B2AR agonists such as salbutamol, salmeterol, formoterol, and terbutaline that can be used are the amounts that are have been approved by the FDA for use in humans.

ARA-211, isoproterenol and other B2AR agonists disclosed herein can be formulated in various forms. In one embodiment, ARA-211 is formulated according to the protocols commonly used by one of skill in the art. The teachings herein are equally applicable for other B2AR agonists. For example, since living cells are to be contacted with ARA-211, one of ordinary skill in the art would formulate ARA-211 in a manner that would not result in harm to the living cells. Accordingly, ARA-211 may be formulated using some or all of the same ingredients that would normally be present in cell culture media for the particular cell type that is being used. In another embodiment, ARA-211 may be formulated in PBS at a dilution that does not harm or affect the biological activity of the cells to which ARA-211 contacts.

The formulation will vary for in vivo administration. One of skill in the art will appreciate the differences between the formulation needed for intravenous administration as contrasted with the formulation that would be optimal for another mode of administration, e.g., topical. As with in vitro protocols, one of ordinary skill in the art would take into consideration the need to formulate ARA-211 in a manner that does not cause toxicity in the individual, damage the individual to any appreciable degree or cause appreciable adverse side effects.

In another embodiment, ARA-211 is formulated according to methods known in the art for similar B2AR agonists, for example, salbutamol, salmeterol, formoterol, and terbutaline (all of which have been approved by the FDA for use in humans).

ARA-211 is administered to individuals in an amount sufficient to achieve the desired beneficial effects. In one embodiment, the desired effect is cessation of tumor growth and/or tumor regression. In another embodiment, the desired effect is inducing apoptosis of cancer cells. In other embodiments, the desired effects are to inhibit the transformation of cells, reduce and/or inhibit the growth of tumors, reduce and/or inhibit metastasis of cancerous cells. A trained clinician would know what indices to observe and adjust the dosages accordingly.

The amount of ARA-211 administered in order to administer an sufficient amount to treat the disease or condition associated with aberrant Raf-1/Mek-1/Erk activity will depend upon a variety of factors, including, for example, the particular cancer being treated, the mode of administration, the severity of the cancer being treated and the age and weight of the patient, the bioavailability of the formulation, the adverse effects experienced by the individual being treated, etc. Determination of an effective dosage is well within the capabilities of those skilled in the art in view of the teachings provided herein. Dosages may also be estimated using in vivo animal models as described in the Examples section.

Diagnostic Uses

The invention also provides methods for diagnosing cancer in an individual. A biological sample is removed from the individual, preferably containing cells. The sample is assayed, using the protocols disclosed herein, to determine if the cells express a B2AR that can be stimulated with an agonist. In addition, the phosphorylation state of the Erk protein is also assessed using the protocols disclosed herein. In cancer cells or tumor cells, the Erk protein tends to be persistently activated in a way that does not require activation via an external stimulus. The presence of activated Erk, shown by detecting a phosphorylated form of Erk (i.e., P-Erk), and the ability to be stimulated via the B2AR pathway are highly indicative that a cell is cancerous. In the alternative, if the cell not cancerous, then it runs a great likelihood of becoming cancerous.

Kits Comprising ARA-211

The invention also provides for kits comprising B2AR agonists, such as ARA-211 or isoproterenol in suitable formulations. The formulations may be in unit dosage amounts. Kits may further comprise suitable packaging and/or instructions for use of ARA-211 in diagnosing and treating diseases or condition associated with aberrant Raf-1/Mek-1/Erk activity. Kits may also comprise a means for the delivery of ARA-211, such as those known to a skilled artisan.

Combination Therapy

Inhibitors of the Raf-1/Mek-1/Erk signaling pathway (e.g., ARA-211) can be administered alone or in combination therapy with other treatments, for example, other B2AR agonists, chemotherapy or radiation therapy. The timing of radiation therapy is generally known by one skilled in the art of radiology and radiation treatment.

For all of the foregoing combination therapies, one of skill in the art would evaluate the progress of such combination therapy by assessing, inter alia, tumor size regression, changes in cell morphology from that of abnormal morphology to normal morphology, decline or inhibition of metastasis, and/or decline or inhibition of angiogenesis. One of skill in the art will be able to recognize other indices that would indicate the positive effects that ARA-211 has on the individual to whom it has been administered.

The following examples are provided to further illustrate the invention; however, they should not be construed to limit the invention in any manner.

EXAMPLES

Example 1

Materials and Methods

The following methods and materials were used for the experiments discussed infra.

Cell Lines and Transfections—All cell lines used were obtained from American Type Tissue Collection (ATCC), (Manassas, Va.), or from the DCTD Tumor Repository, (Frederick, Md.). Propagation was carried out according to ATCC protocols. Propagation media was obtained from Invitrogen Corporation (Carlsbad, Calif.). DNA transfections were carried out using TransIT-LT1 transfection reagent (Takara Mirus, Madison, Wis.) according to the manufacturer's protocol. Briefly, $4 \times 10^5$ MDA-MB-231 cells were grown to approximately 70% confluency in medium supplemented with 10% FBS (Atlanta Biologicals, Atlanta, Ga.) in the absence of antibiotics. For transfection, LT1 was pre-incubated in 200 μl per transfection in Opti-MEM (Invitrogen) for 20 minutes prior to addition of plasmid. 2 μg of plasmid DNA (pFC-MEKK Stratagene, La Jolla, Ca.) per transfection was incubated with the Opti-MEM/LT1 mixture for 20 minutes after which the transfection mixture was added to cells and incubated at 37° C. for 48 hours. At that time, cells were then treated with either DMSO or ARA-211 (10 μM) for 48 hours and subsequently assayed for proliferation via Alamar Blue metabolism and harvested for western blot analysis as described below.

Cytoblot screening for small molecules that decrease phospho-Erk 1/2—MDA-MB-231 cells were plated into sterile, white opaque, 96 well tissue culture plates at a density of 25,000 cells/well, cells were allowed to attach overnight and were treated for 1 hour in the presence of either vehicle control, 20 μM PD-98059 (EMD Biosciences, San Diego, Calif.), or 10 μM of NCI Diversity Set of 2000 compounds (1compound/well) (<http://dtp.nci.nih.gov/>) as described by us (Blaskovich et al., 2003). Cells were then washed, fixed for one hour at 4° C. cold 3.7% formaldehyde and permeabilized for 5-min with ice-cold methanol. Cells were washed, and rocked overnight at 4° C. with anti-phospho-p44/42 MAPK (Cell Signaling Technology, Beverly, Mass.) and Horse Radish Peroxidase conjugated anti-Rabbit IgG secondary antibody (Jackson ImmunoResearch, West Grove, Pa.). The plates were washed and chemiluminescence reagent added to the wells of the plates, then x-ray film directly placed on top of the plates. Quantification of the results was done using a GS-700 scanning densitometer (Bio-Rad Laboratories, Hercules, Calif.).

Western Blotting—Treated cell samples were lysed in 30 mM HEPES, 10 mM NaCl, 5 mM $MgCl_2$, 25 mM NaF, 1 mM EGTA, 1% Triton-X-100, 10% Glycerol, 2 mM Sodium orthovanidate, 10 μg/mL aprotinin, 10 μg/mL soybean trypsin inhibitor, 25 μg/mL leupeptin, 2 mM phenylmethylsulfonylfluoride (PMSF), 6.4 mg/mL p-nitrophenylphosphate for 30 minutes at 4° C., and proteins run on SDS-PAGE gels then transferred to nitrocellulose membranes. Membranes were blocked in either 5% milk in PBS, pH 7.4, containing 0.1% Tween-20 (PBS-T) or 1% BSA in TBS, pH 7.5, containing 0.1% Tween-20 (TBS-T). Phospho-STAT3 and phospho-AKT antibodies were diluted in 1% BSA in TBS-T while phospho-c-Raf, phospho-Mek, and phospho-p44/p42 MAPK antibodies (Cell Signaling) were diluted in 5% milk in PBS-T for either 1 hour at room temperature or overnight at 4° C. HRP-conjugated secondary antibodies (Jackson ImmunoResearch, West Grove, Pa.) were diluted in 5% milk in PBS-T or TBS-T at a 1:1000 dilution for one hour at room temperature. Western blots results were visualized using enhanced chemiluminescence. Stripping of the membranes for reblotting was done using stripping buffer (62.5 mM Tris pH 7.6, 2% SDS, 0.7% 2-mercaptoethanol) at 50° C. for 30 minutes.

In Vitro Kinase Assays—MDA-MB-231 cells ($2 \times 10^6$) were lysed for 30 minutes at 4° C. in RIPA-150 buffer (10 mM Tris pH 7.5, 150 mM NaCl, 10% glycerol, 5 mM EDTA, 1% Triton X-100, 0.1% SDS, 100 μM sodium orthovanadate, 1 μM aprotinin, 10 μM leupeptin, 10 μM antipain). Cell debris was pelleted at 13000 rpm for 15 minutes at 4° C. and the lysate was rocked overnight with 10 μg of either c-Raf or MEK antibodies (Santa Cruz Biotechnologies, Santa Cruz, Calif.). 25 μl of protein A/G PLUS agarose (Santa Cruz Biotechnology) was then added and rocked for 4 hours at 4° C. Samples were spun at 2000 rpm for 5 minutes to collect the agarose beads, which were then washed four times with lysis buffer. On the final wash each pellet was divided into 5. Pellets were resuspended in 30 μl kinase buffer (30 mM HEPES, pH 7.5, 7 mM $MnCl_2$, 5 mM $MgCl_2$, 1 mM dithiothreitol and 15 μM adenosine triphosphate (ATP) with either 10 µM U-0126 (EMD Biosciences) ARA-211, Raf Kinase Inhibitor (EMD Biosciences), or DMSO vehicle control. Finally, 0.5 µg MEK-1 or Erk-2 peptide substrate (Upstate Biotechnologies, Lake Placid, N.Y.) was added, followed by 20 µCi [$\gamma$-$^{32}$P]-ATP per sample. Samples were then incubated at room temperature for 30 minutes and the reaction terminated by the addition of 30 µl 4×SDS-PAGE sample buffer (33% glycerol, 0.3 M DTT, 6.7% SDS, 15% β-mercaptoethanol, 0.1% bromphenol blue), which was then boiled at 100° C. for 5 minutes. Samples were run on a 10% polyacrylamide gel to separate proteins; gels were dried and phosphorylatlion results visualized via autoradiography.

In Vivo Kinase Assay—Intact MDA-MB-231 cells ($2\times10^6$) were treated either with vehicle control (DMSO), 10 µM U-0126, 10 µM Raf Kinase Inhibitor, or 10 µM ARA-211. Samples were then processed for kinase assays as described above.

MTT Assay—2000 cells per well were plated into 96 well tissue culture plates, and the cells were allowed to attach overnight at 37° C. with 10% $CO_2$. Cells were then treated with increasing concentrations of ARA-211, or vehicle (DMSO) and incubated for four days. At that time treatment medium was removed and replaced with 100 µl of lmg/ml MTT (Sigma-Aldrich, St. Louis, Mo.) in media and incubated at 37° C., 10% $CO_2$ for 3 hours. After 3 hours the MTT media was removed and replaced with 100 µl/well of DMSO, rocked at room temperature for 5 minutes, then absorbance read at 540 nm on a micro-plate reader.

Alamar Blue proliferation assay—For proliferation assays using exogenous constitutively activated MEK or the B2AR antagonist ICI-118.551, Alamar Blue metabolism assay used to determine cell viability according to the manufacturers protocol (Biosource, Camarillo, Calif.). Briefly, cells were treated and grown as described above; Alamar Blue was added to the media at a 1:10 dilution and incubated for 3 hours. Media/Alamar Blue was removed from the cells and aliquoted into 96 well plates (100 µl per well) and fluorescence read on a Wallac Victor 2 plate reader at excitation 540 nM, and emission 615 nM.

Soft Agar Assay—Anchorage independent growth assays were performed as previously described (Lerner et al., 1997). Briefly, agar was diluted to 0.3% in propagation media containing 20,000 cells and either vehicle or ARA-211 and 1 ml of cell/agar mixture plated on top of 2 ml of a 0.6% layer of agar in medium alone. Cells were grown for three to four weeks at 37° C., 10% Co2 and were fed weekly with 100 µl per well of media/treatment. Quantification of colonies was done using a GS-700 scanning densitometer.

Apoptosis Assay—Apoptosis was analyzed using the Cell Death Detection ELISA (Roche, Indianapolis, Ind.) measuring cytoplasmic histone-associated mono- and oligonucleosome DNA fragments. Procedures were carried out according to the manufacturers protocol. Briefly, $1\times10^5$ cells were plated in 60 mm dishes and treated with various doses of ARA-211 or vehicle for 48 hours. Cells were lysed with the provided lysis buffer and lysate was incubated on the ELISA plate for 1 hour to capture the histone associated DNA indicative of apoptotic cells. Anti-DNA peroxidase conjugated antibody was added to detect the cleaved DNA and the microplate was washed and developed with ABTS substrate which was quantitated by microplate reader at 405 nm.

Total cellular cAMP measurement—The measurement of total cellular cAMP was done using a cAMP Biotrak ™ Enzymeimmunoassay (EIA) system (Amersham Biosciences, Piscataway, N.J.) according to the manufacturer's protocol. Briefly, 2000 cells were plated into each well of a 96 well plate. The next day cells were treated with increasing concentrations of ARA-211 or with vehicle for one hour. Alternatively, MDA-MB-231 cells were pre-treated with antagonists to the α1 (Prazosin, Sigma), α2 (Yohimbine, Sigma), β1 (Metoprolol, Sigma), and β2 (ICI 118.551, Sigma) adrenergic receptors at 100 nM for 15 minutes followed by treatment with 10 µM ARA-211 for 45 minutes. Cells were then lysed directly in the wells using the supplied lysis buffer. The lysate was transferred to a 96-well cAMP ELISA plate, and results were quantified using a Wallac Victor 2 plate reader.

PKA Kinase Assay—PKA kinase assays were performed with the SignaTECT® cAMP-Dependent Protein Kinase (PKA) Assay System (Promega, Madison Wis.) according to the manufacturer's protocol. Briefly, cells were plated ($5\times10^6$) into 100 mm dishes and treated the next day with ARA-211, H-89 (EMD Biosciences), or vehicle. Cells were lysed using a Dounce homogenizer and lysates were incubated in the supplied kinase reaction buffer, with $^{32}$P-ATP and biotin labeled PKA peptide substrate for 5 min at 37° C. Once the reactions were quenched they were spotted onto streptavidin membranes and $^{32}$P-ATP transfer was measured via scintillation counter.

Anti-tumor activity in nude mouse xenograft model—Female athymic nude (nu/nu) mice, 5-6 weeks old, were purchased from Charles River (Wilmington, Mass.) and allowed to acclimate in the animal facility for one week. After harvesting, A-549, SNB-19, ACHN, and HCT-116 cells were, resuspended in sterile PBS, and injected s.c. into the right and left flanks ($10\times10^6$ cells per flank) of the mice as previously described (Sun et al., 2005). For MDA-MB-231, cells were harvested and resuspended in PBS ($10\times10^6$ cells per 50 µl) and an equal volume of Matrigel (BD Biosciences, San Jose, Calif.). 100 µl of MDA-MB-231 cells in PBS/Matrigel were injected s.c. into the mammary fat pads between the $2^{nd}$ and $3^{rd}$ nipples on each side of the mice. Once the tumors reached approximately 200-300 mm$^3$ the mice were randomized and treated i.p. with 0.1 ml vehicle (PBS) or ARA-211. Each treatment group consisted of five mice (2 tumors per mouse, a total of 10 tumors). The tumor volumes were determined by measuring the length (l) and width (w) and calculating the volume ($V=w^2l/2$). Statistical significance between the control and treated animals was determined using a student's t test.

Immunohistochemisty (IHC) and slide quantitation—Upon completion of the xenograft study, mice were euthanized and the tumors were removed and fixed in 10% buffered formalin for at least 24 hours. Three tumors per treatment group were then prepared and stained for proliferation marker Ki-67, apoptosis by TUNEL, and phosphor-Erk 1/2 as previously described (Sun et al., 2003). The IHC slides were analyzed at the Analytical Microscopy Core facility of the H. Lee Moffitt Cancer Center & Research Institute. The Ariol SL-50 automated image analysis system (Applied Imaging, Santa Clara, Calif.) was used for quantitation of each slide as previously described (Jiang et al., 2004). Briefly, high-resolution digital pictures were taken of the entire stained area of each slice of tumor tissue for automatic staining quantitation. Two thresholds were used to signify positive staining, one recognizing background and one recognizing positive brown staining. The percentage of positive staining was calculated by dividing the positive staining by the total staining (positive+negative) divided by the total area stained, and the intensity of the stain was determined by calculating the integrated optical density of the positive stain with the negative background stain subtracted out. Each slide analyzed consisted of 54,000 to 160,000 cells analyzed depending on the size of the tumor when resected. Significance of the quantitation was analyzed by a two-tailed student's t-test.

Example 2

HTS of the NCI Diversity Set Identifies ARA-211, as a Potent Inhibitor of P-Erk 1/2 and P-Mek but not P-JNK, p38, P-Akt and P-STAT3 Levels in Human Cancer Cells

Many common genetic alterations in human cancers result in the hyperactivation of the kinase Mek-1 leading to constitutively phosphorylated Erk 1/2. Because aberrant activation of the Mek-1/Erk 1/2 pathway has been implicated in oncogenesis and tumor survival, we sought to identify molecules that thwart this pathway. To this end, we first used a chemical biology approach by screening a 2,000 compound library (the NCI diversity set) from the National Cancer Institute for pharmacological agents capable of suppressing the levels of P-Erk 1/2 in the human breast cancer cell line MDA-MB-231. Treatment of MDA-MB-231 cells with compounds from the NCI diversity set (96 well plate assay, 1 compound (10 µM) per well) for 4 hours and subsequently processing the plates for a cytoblot using an antibody specific for P-Erk 1/2, resulted in several compounds that suppress P-Erk 1/2 levels. One of these, ARA-211 (FIG. 1A) suppressed potently at 10 nM the levels of P-Erk 1/2 without affecting the levels of total Erk 1/2. ARA-211 also suppressed P-Mek-1 levels but not P-c-Raf-1, P-JNK, P-p38, P-Akt and P-STAT3 (FIG. 1B). These results demonstrated that ARA-211 is selective for disrupting the Mek-1/Erk 1/2 but not other oncogenic and tumor survival pathways.

Example 3

ARA-211 Inhibits Mek-1 and c-Raf-1 Kinase Activities in Whole Cells but not in vitro

The fact that ARA-211 suppressed the levels of P-Mek-1 and P-Erk 1/2 suggested that it might be a c-Raf-1 kinase inhibitor. In vitro incubation of c-Raf-1 and Mek-1, immunoprecipitated from MDA-MB-231 cells, with ARA-211 did not inhibit c-Raf-1 and Mek-1 kinases (FIG. 1C). As expected, the c-Raf-1 kinase inhibitor (Rki) and the Mek-1 inhibitor (U-0126) blocked in vitro c-Raf-1 and Mek-1 kinase activities, respectively (FIG. 1C). In contrast to the in vitro studies, c-Raf-1 and Mek-1 kinase activities were blocked by ARA-211 when intact MDA-MB-231 cells were first treated with ARA-211 (FIG. 1D).

ARA-211 is a β2 adrenergic receptor agonist that disrupts the c-Raf-1/Mek-1/Erk 1/2 pathway by increasing cAMP levels, activating PKA and inhibiting c-Raf-1 kinase activity. The fact that ARA-211 inhibits c-Raf-1 and Mek-1 kinase activities when intact cells are treated but not in vitro suggested that the target for this compound is upstream of c-Raf-1 kinase. An ACS chemical library search identified ARA-211 as Pirbuterol, a beta adrenergic receptor agonist. To demonstrate that ARA-211 acts as a β adrenergic receptor agonist in MDA-MB-231 cells and that this results in blockade of the Raf/Mek/Erk pathway, we treated these cells with ARA-211 and first showed that this compound induced the formation of CAMP (FIG. 2A). We then determined that ARA-211 is highly selective for β2 adrenergic receptors by determining that only β2 but not β1, α1 or α2 receptor antagonist, blocks the ability of ARA-211 to induce cAMP formation (FIG. 2A). The increase in CAMP resulted in activation of protein kinase A (PKA), which also required β2 AR stimulation as pre-treatment of MDA-MB-231 cells with β2 AR specific antagonist prevented ARA-211 from activating PKA (FIG. 2B). We then demonstrated that the ability of ARA-211 to disrupt the c-Raf-1/Mek-1/Erk 1/2 pathway requires its ability to stimulate the β2 adrenergic pathway by demonstrating that the β2 adrenergic receptor antagonist ICI 118, 551, prevented ARA-211 from suppressing P-Erk 1/2 levels (FIG. 2C).

Example 4

ARA-211 inhibits Tumor Cell Growth and Induces Apoptosis only in Human Cancer Cells where it can Stimulate the β2 Adrenergic Receptor

Figure 2:
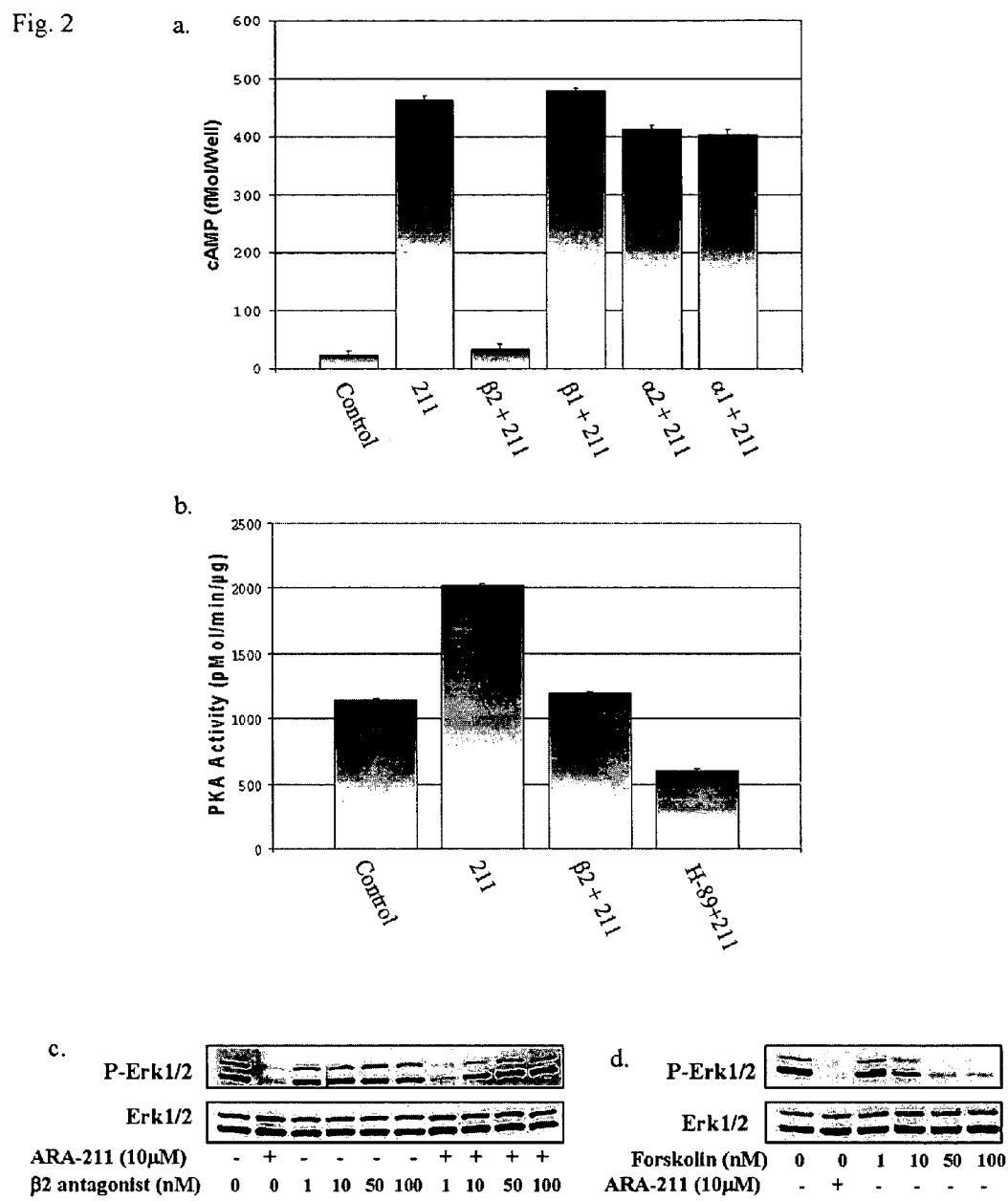
FIG. 2 depicts results that show that B2AR stimulation, cAMP increase and PKA activation decrease P-Erk 1/2 levels. MDA-MB-231 cells were treated with ARA-211 alone or in the presence of β1, β2, α1 or α2 adrenergic receptor antagonists and the levels of cAMP (a), PKA (b) and P-Erk 1/2 (c) were determined as described under Materials and Methods. MDA-MB-231 cells were also treated with the adenylyl cyclase activator forskolin and its effects on P-Erk 1/2 levels determined (d). All experiments are representative of at least 2 independent experiments.
Figure 3A:
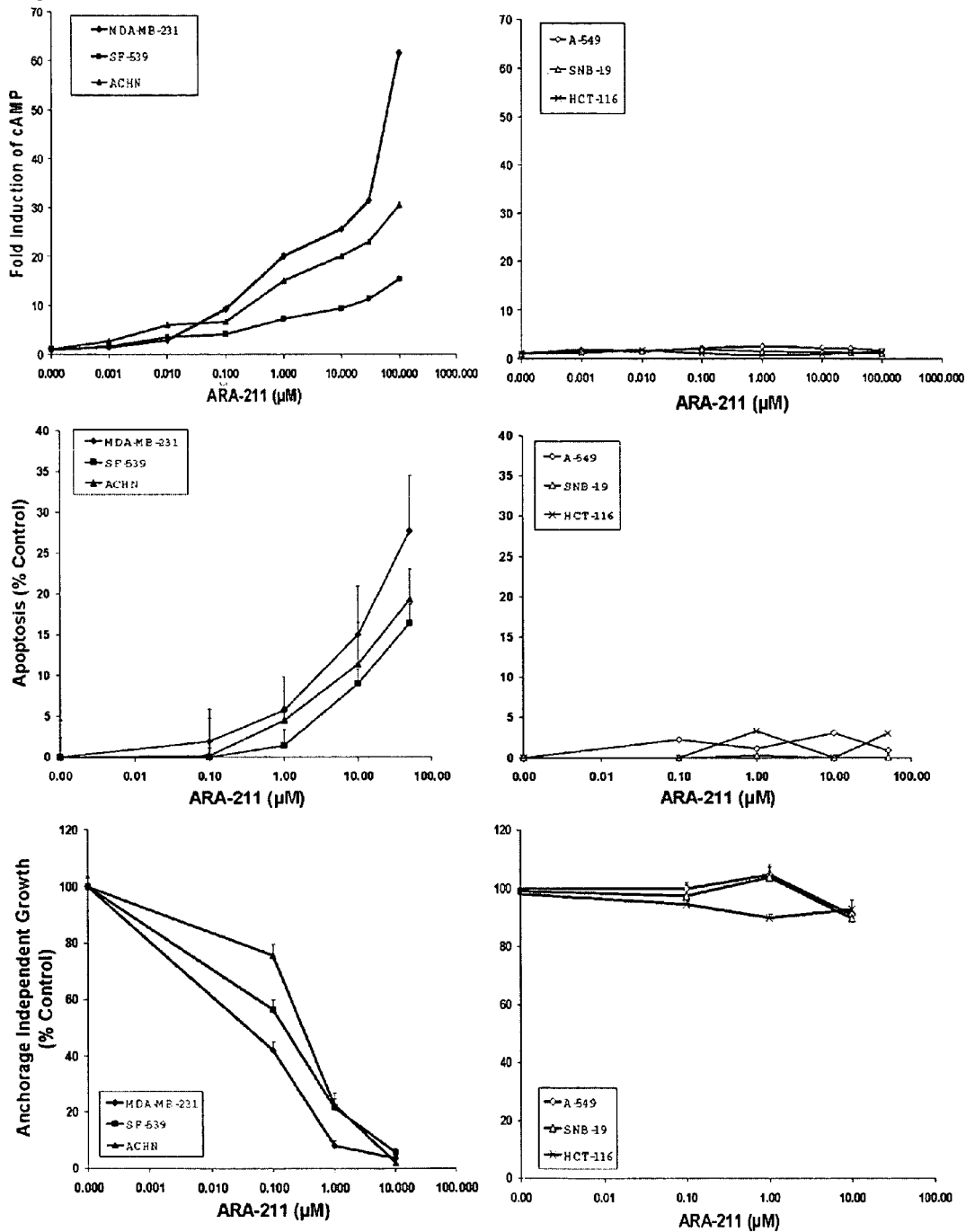
FIG. 3 depicts the results showing that ARA-211 inhibits tumor cell growth and induces apoptosis by β2AR-stimulation of cAMP and inhibition of Mek1. (a) ARA-211 inhibits cell growth and induces apoptosis only in human cancer cells where it induces cAMP production. MDA-MB-231, SF-539, ACHN, A-549, SNB-19 and HCT-116 were treated with various concentrations of ARA-211 and the levels of cAMP, apoptosis and anchorage-independent growth were determined as described under Materials and Methods. (b and c) MDA-MB-231 cells were treated with ARA-211 alone or in the presence of the β2AR antagonist ICI 118.551 (b) or CA-Mek (c) and the effects of treatment on tumor cell growth and P-Erk 1/2 levels were determined as described under Materials and Methods. All experiments are representative of at least 2 independent experiments.
Figure 3B:
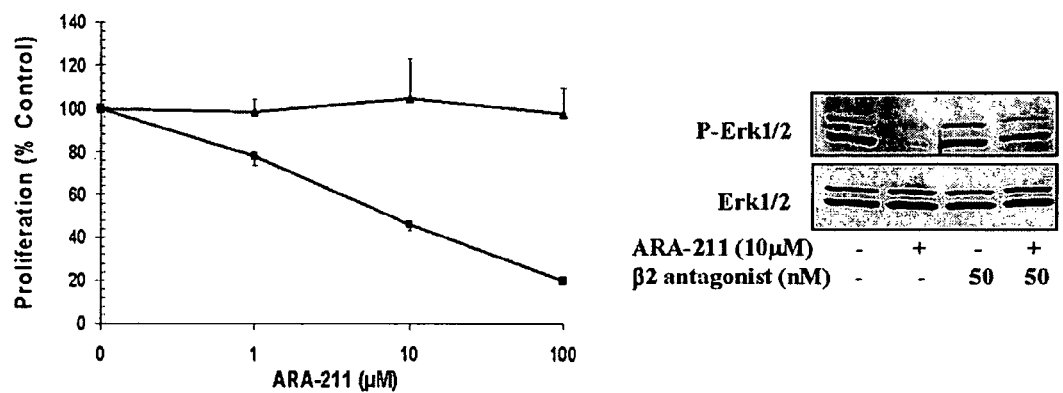

The data from FIGS. 1 and 2 demonstrated that stimulation of the β2 AR is required for ARA-211 to suppress the c-Raf-1/Mek-1/Erk 1/2 pathway. We next determined whether activation of the β2 adrenergic receptor and inhibition of the c-Raf-1/Mek-1/Erk 1/2 pathway results in inhibition of tumor cell growth and survival of human cancer cells. To this end we first used a panel of 7 human cancer cell lines, three where ARA-211 inhibits P-Erk 1/2 levels (MDA-MB-231 (breast), SF-539 (CNS) and ACHN (renal)) and 4 where it did not (A-549 (lung), HCT-116 (colon), SNB-19 (CNS) and MCF-7 (breast)). FIG. 3A and Table 1 show that P-Erk 1/2 levels were suppressed only in the human cancer cell lines where ARA-211 induced cAMP production. Furthermore, ARA-211 potently inhibited anchorage-dependent and independent growth and induced apoptosis in cell lines where it stimulated the β2 AR and inhibited P-Erk 1/2 but not in cell lines where it did not (FIG. 3A and Table 1). To further demonstrate that the ability of ARA-211 to inhibit tumor cell growth requires stimulation of the β2 AR we showed that the β2 AR antagonist ICI 118, 551 rescued human cancer cells from ARA-211 inhibition of tumor cell growth (FIG. 3 B).

TABLE 1

|  | MDA-MB-231 | SF-539 | ACHN | A-549 | HCT-116 | SNB-19 |
|---|---|---|---|---|---|---|
| cAMP (Fold Induction) | 16.7 ± 5.4 | 13.1 ± 3.0 | 16.5 ± 3.2 | 1.3 ± 0.3 | 1.1 ± 0.1 | 1.2 ± 0.4 |
| P-Erk ½ (% Inhibition) | 100% | 100% | 91% | 0% | 0% | 0% |
| Anchorage Dependent Growth (% Inhibition) | 60.6 ± 6.5 | 55 ± 6.9 | 62 ± 12.7 | 9.6 ± 6.1 | 6.5 ± 4 | 0 (n = 3) |
| Anchorage Independent Growth (% Inhibition) | 82.7 ± 7.9 | 94.4 ± 1.5 | 97.9 ± 1.2 | 0 (n = 6) | 7.3 ± 3.1 | 5.1 ± 5.0 |
| Apoptosis (% Induction) | 15 ± 4 | 9 ± 1.7 | 11.4 ± 1.9 | 3.1, 2.2 | 0, 1.2 | 0, 0 |

Table 1 shows that ARA-211 inhibits anchorage-dependent and -independent tumor cell growth and induces apoptosis only in human cancer cells where it induces cAMP production and inhibits P-Erk 1/2 levels. All methods are as described in the Methods and Materials section.

Figure 3C:
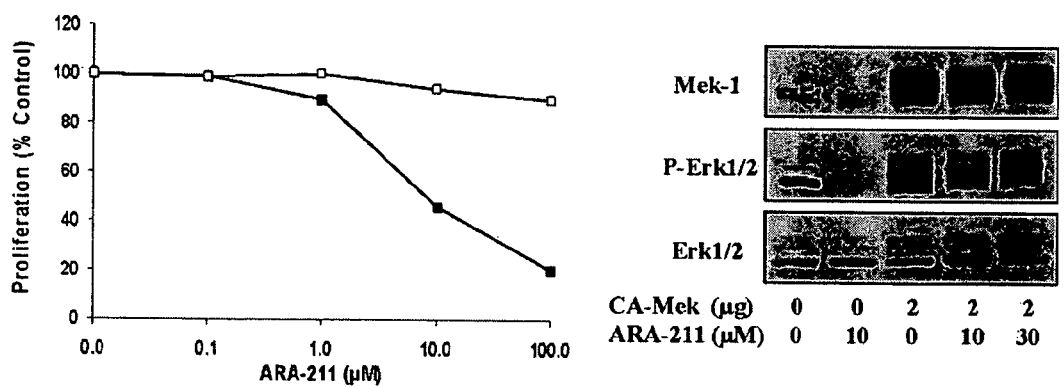

Example 5

β2 Adrenergic Stimulation Requires Inhibition of Mek-1 to Suppress P-Erk 1/2 Levels and to Inhibit Tumor Cell Growth The above date clearly demonstrated that the ability of ARA-211 to disrupt the c-Raf-1/Mek-1/Erk 1/2 pathway and to inhibit tumor cell growth and survival depends on its ability to stimulate the B2AR. However, the ability of ARA-211 to inhibit tumor cell growth could be due to its ability to affect cellular events other than those leading to decreased P-Erk 1/2. Therefore, we next determined whether the inhibition of tumor cell growth by ARA-211 requires its ability to inhibit the c-Raf-1/Mek-1/Erk 1/2 pathway. We reasoned that if suppression of c-Raf-1 and Mek-1 are critical to ARA-211 inhibition of tumor growth then ectopically expressing constitutively activated Mek-1 would rescue human cancer cells from the effects of ARA-211. FIG. 3C shows that MDA-MB-231 cells that ectopically express constitutively activated Mek-1 are resistant to APA-211 inhibition of P-Erk 1/2 and inhibition of tumor growth.

Example 6

β2 Adrenergic Stimulation Causes Regression of Human Tumors in Animal Models

Figure 4:
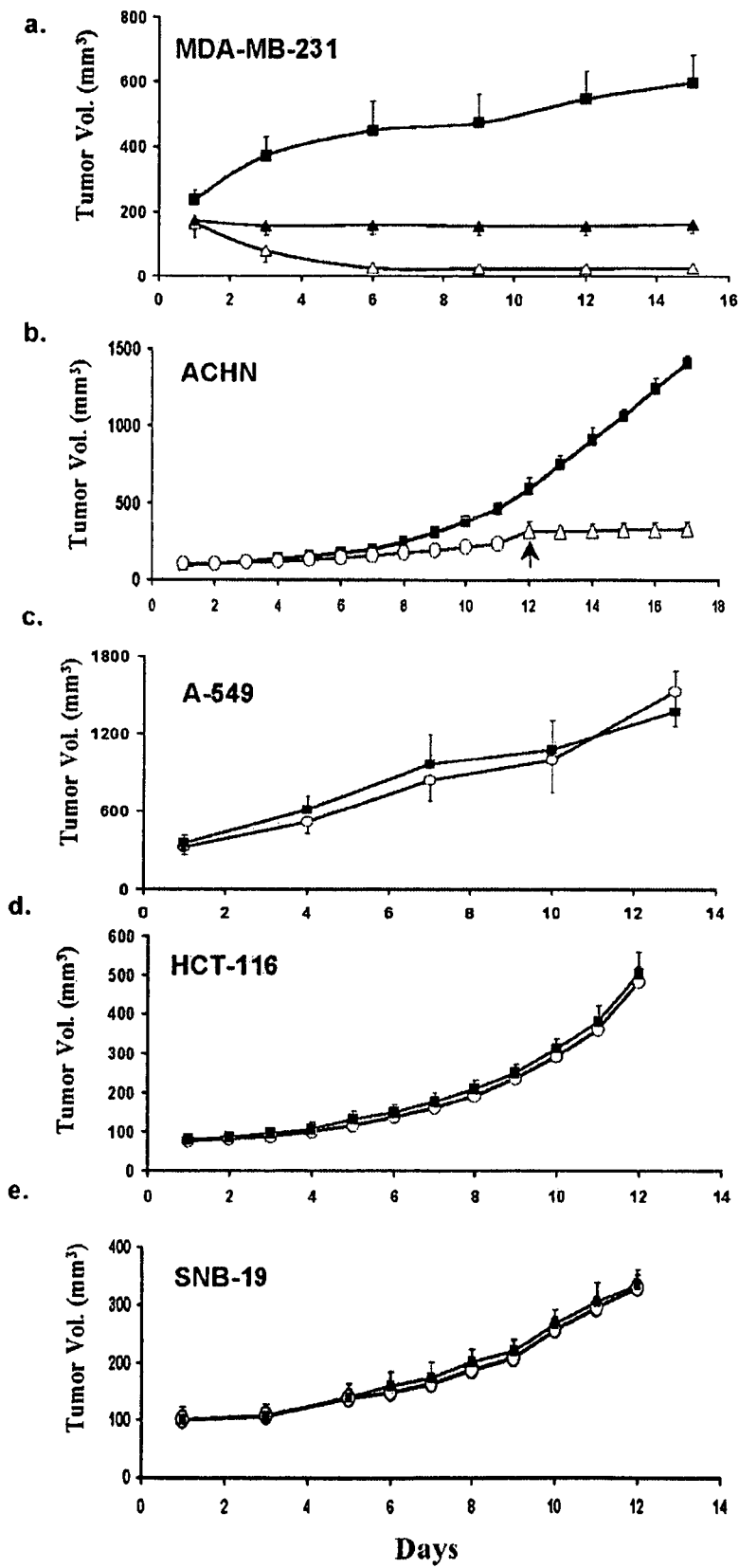
FIG. 4 depicts results that show that ARA-211 suppresses tumor growth and causes tumor regression. MDA-MB-231 cells (a) were implanted under mammary fat pads, and ACHN (b), A-549 (c), HCT-116 (d) and SNB-19 (e) were implanted s.c. in nude mice and the mice treated (i.p.) either with vehicle (■) or ARA-211, 100 mpk/day (MDA-MB-231, ▲), 200 mpk/day (MDA-MB-231, Δ), 75 mpk/day (○, ACHN, A-549, HCT-116 and SNB-19) or 200 mpk/day (ACHN stating day 12, see ↑) as described under Materials and Methods. MDA-MB-231 and A-549 data are representative of three independent experiments, while ACHN, HCT-116, and SNB-19 data are from 1 experiment.
Figure 5:
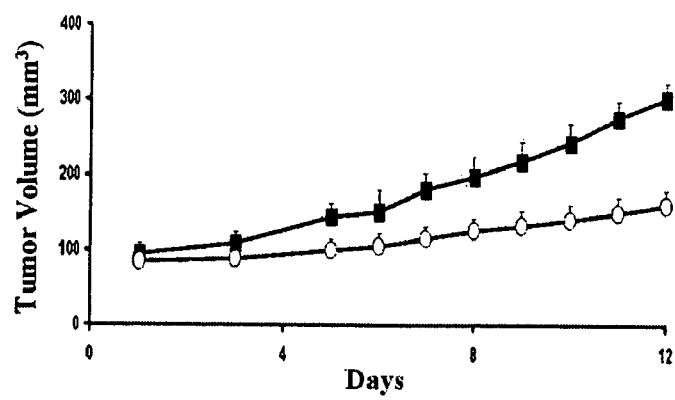
FIG. 5 depicts results that show that ARA-211 suppresses P-Erk 1/2 levels, inhibits tumor cell growth and induces apoptosis in human xenografts in nude mice. MDA-MB-231 cells were implanted under mammary fat pads and the mice treated with vehicle (■) or ARA-211 (○, 75 mpk/day) as described under FIG. 4, tumors removed on day 12 and processed for P-Erk 1/2 levels (IHC), apoptosis (Tunel) and proliferation (Ki-67) as described under Materials and Methods. Pictures represent 1/100 of the total slide area analyzed for one of the three samples per treatment group.
Figure 5:
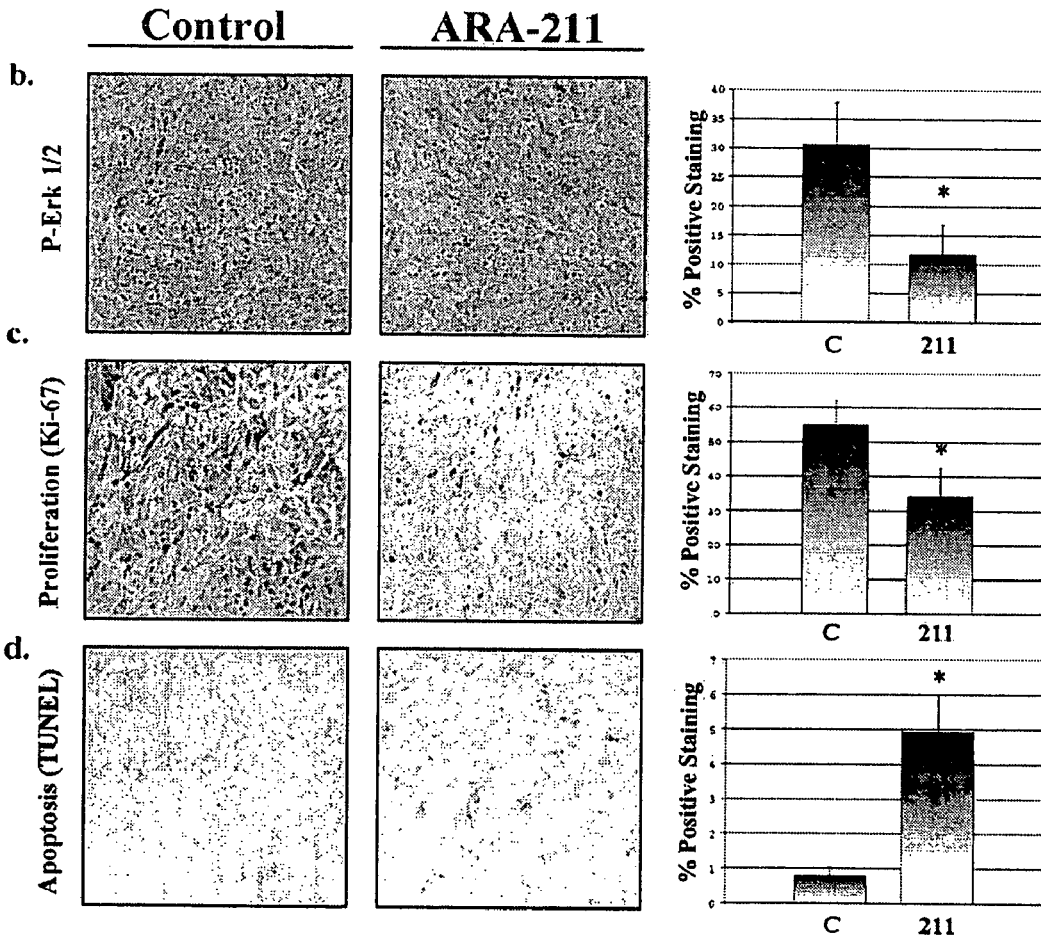

The ability of ARA-211 to inhibit tumor cell growth and induce apoptosis in cultured cells in a B2AR and Mek-1-dependent manner, suggested that ARA-211 may induce tumor regression in human cancers where it can block the c-Raf-1/Mek-1/Erk 1/2 pathway. We, therefore, determine the ability of ARA-211 to interfere with the growth and progression in nude mice of several human tumor types. FIGS. 4C, D, and E show that the growth of tumors where ARA-211 does not stimulate cAMP and decrease P-Erk 1/2 (e.g., SNB-19, HCT-116 and A-549) is not affected by treatment i.p. with ARA-211 (75 mpk/day). In contrast, FIGS. 4A and B show that the growth of tumors where ARA-211 stimulate cAMP and inhibit P-Erk 1/2 levels (e.g., ACHN and MDA-MB-231) was inhibited by the same treatment. Furthermore, increasing the dose of ARA-211 to 200 mpk/day suppressed tumor growth of ACHN and caused tumor regression in MDA-MB-231 tumors (FIGS. 4A and B).

Example 7

Stimulation of the B2AR Results in Rap-1 Activation

The effect of B2AR stimulation on Rap1 was investigated using the following methods: A Rap-1 activation assay kit (Upstate, Temecula, Calif.) was used according to protocol to determine if stimulation of the B2AR by ARA-211, and subsequent downstream signaling resulting in inhibition of P-Erk 1/2, is mediated by activation of Rap-1 directly by the Rap-1 guanine nucleotide exchange factor Epac. Briefly, $1\times10^6$ ACHN cells were plated and allowed to attach over night, and then treated with either vehicle (DMSO), 10 μM ARA-211, 10 μM specific EPAC activator 8-pCPT-2'-O-Me-cAMP, 10 μM isoproterenol, 10 μM forskolin, 1 μM 8Br-cAMP, 10 μM PKA kinase inhibitor H89, pre-treatment with 10 μM H89 (1 hr) followed by ARA-211 treatment, and a dish with cells only was used for lysate for positive control (GTP-C). Cells were incubated with drugs for 1 hour unless noted otherwise. Cells were then lysed, the positive control lysate was incubated with 10 mM EDTA and 100 μM GTPγS and incubated for 30 minutes to load GTP onto Rap-1. Lysates from all samples were then incubated with 25 μg GST-RalGDS-Rap-1 binding domain beads for 45 minutes, washed with assay buffer 3×, resuspended in 40 μl of 2×Laemmli sample buffer and boiled for 5 minutes. Samples were resolved by SDS-PAGE electrophoresis, transferred to nitrocellulose, blotted overnight with 1 μ/ml polyclonal anti-Rap-1, and visualized by chemiluminescence.

Figure 6:
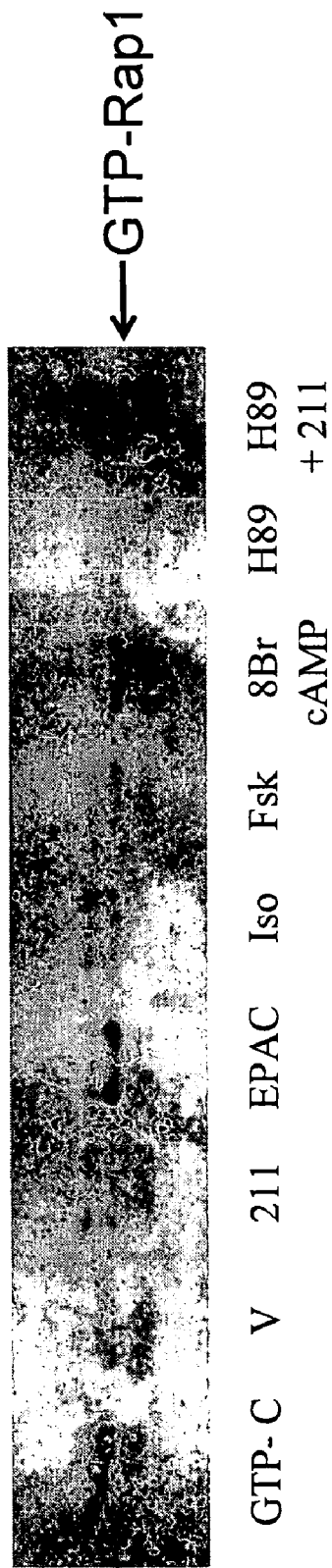
FIG. 6 depicts results that show that ARA-211 and an Epac activator activate Rap1 which is implicated in the inhibition of Raf-1 kinase activity. The experimental methods used for this set of experiments are described in Example 7. Briefly, ACHN cells were treated with various compounds and the lysates of the cells were incubated with EDTA and GTPγS and then further incubated to load the GTP onto Rap-1. Then the lysates were incubated with binding domain beads and run on a gel. The gel is shown in FIG. 6. The lane designations are as follows: "GTP-C" refers to the positive control. "V" refers to treatment with a vehicle (DMSO). "211" refers to treatment with ARA-211. "EPAC" refers to treatment with a specific Epac activator 8-pCPT-2'-O-Me-cAMP. "Iso" refers to treatment with isoproterenol. "Fsk" refers to treatment with forskolin. "8Br cAMP" refers to treatment with 8Br-cAMP. "H89" refers to treatment with the protein kinase A inhibitor H89. "H89+211" refers to treatment first with H89 followed by treatment with ARA-211.

The results are depicted in FIG. 6. GTP-loaded Rap-1 is visualized at ~25 KDa as determined by the positive control for GTP-Rap-1 (GTP-C). ARA-211 along with the EPAC activator, isoproterenol, forskolin, and 8Br-cAMP all activated Rap-1, some more potently than others. DMSO (V) and H89 had no effect on Rap-1 activation, more importantly, blocking PKA kinase activity had no effect on the ability of ARA-211 to stimulate Rap-1 activation. This data, taken together with previous findings, shows that stimulation of the B2AR results in Rap-1 activation in a PKA independent manner, thus implicating Epac as the major mechanism that results in Rap-1 activation resulting in competition for Ras binding sites and inhibition of Raf-1 kinase activity. In sum, since the stimulation of the B2AR resulted in Rap-1 activation, it implicates Epac as a mechanism that results in activated Rap-1 which competes for Ras binding sites and inhibition of Raf-1 kinase activity.

In view of the foregoing, the present invention provides a chemical biology approach to investigate aberrant signal transduction circuits about the importance of the β2 adrenergic receptor in regulating tumor cell division, survival, metastasis and angiogenesis. The data provided herein demonstrated that activation of the β2 adrenergic receptor results in inhibition of proliferation, induction of apoptosis, suppression and/or regression of human tumors where stimulation of the β2AR results in blockade of the c-Raf-1/Mek-1/Erk 1/2 pathway. This is an important finding as the majority of human cancers harbor genetic alterations that ultimately result in hyperactivation of the c-Raf-1/Mek-1/Erk 1/2 pathway. For example, it is estimated that 30% of all human cancers contain Ras mutations that lead to hyperactivation of this pathway (4). Similarly, a great majority of human cancers over express or contain constitutively activated receptor and non-receptor tyrosine kinases and/or growth factor autocrine loops that also result in hyperactivation of the c-Raf-1/Mek-1/Erk 1/2 (22-25). More importantly, hyperactivation of this pathway is critical to the growth and survival of human tumors (8, 14). Finally, thwarting this pathway in human cancers may result in great benefits in the treatment of cancer patients since the genetic aberrations (e.g., Ras mutations, EGF-R and Erb β2 over expression) that result in hyperactivation of the c-Raf-1/Mek-I/Erk 1/2 pathway have all been associated with poor prognosis, resistance to therapy and shortened patient survival time (11, 12).

Using β2 stimulation to cause tumor regression by blocking the c-Raf-1/Mek-1/Erk 1/2 pathway is a novel and powerful approach that could have a widespread use in cancer therapy. Indeed tumors activate this pathway with a broad spectrum of growth factors/cytokines and their receptors. For example, many growth factors such as EGF, PDGF, FGF, VEGF, IGF-1, heregulin and others all activate this pathway (8, 22, 26, 27). Therefore, tumors that express two or more of these growth factors may require a cocktail of anticancer drugs. In contrast, B2AR stimulation will block activation of the c-Raf-1/Mek-1/Erk 1/2 pathway when it is driven by several growth factors since they all required Mek to activate Erk 1/2 (20, 21, 28-31). Consistent with this, we have shown that growth factor (e.g., EGF) stimulation of P-Erk 1/2 is blocked by ARA-211 in MDA-MB-231 cells.

In one embodiment, this approach is applicable to all tumors and cancer cells that express the B2AR and where stimulation of this receptor results in blockade of c-Raf-1/Mek-1/Erk 1/2 pathway. While in normal cells it has been shown that adrenergic stimulation can either activate or inhibit P-Erk 1/2 and proliferation (21, 29, 32), in tumor cells, it is not known if stimulation of the B2AR can stimulate tumorigenesis. In normal cells, where B-Raf is expressed, β2 adrenergic receptors stimulate Erk 1/2 by activating B-Raf which in turn activate Mek-1 (33, 34). In contrast, some β2 adrenergic receptors inactivate Erk 1/2 by blocking c-Raf-1 (35-38). Therefore, β2 adrenergic receptors may also inhibit or stimulate Erk 1/2 and proliferation in tumors and this may depend on the expression levels of not only the B2AR but also c-Raf-1 and B-Raf.

The inventor has analyzed lysates from the NO 60 cell line panel and found that 52% of the cells express B2AR, 56% express c-Raf-1 and 63% express B-Raf. In this 60 cell line panel, melanoma cell lines express B-Raf but not C-Raf and little B2AR and contain high levels of P-Erk 1/2. Treatment of these cell lines with ARA-211 is not expected to increase P-Erk 1/2. As such, the molecular fingerprint of these cancer cells provides a method for diagnosing cancer by using biological samples from an individual. Thus, it is desirable to determine expression levels of B2AR, c-Raf-1 and B-Raf in fresh human tumor biopsies.

The fact that ARA-211 has previously been used locally and orally (39, 40) in patients with respiratory ailments or cardiac infirmities to evaluate its potential as an anti-asthmatic and anti-hypertensive agent, respectively, will facilitate its testing as an anti-cancer drug in patients with tumors where B2AR stimulation is anticipated to block c-Raf-1/Mek-1/Erk 1/2.

FULL CITATIONS FOR SCIENTIFIC REFERENCES

1. D. Hanahan, R. A. Weinberg, *Cell* 100: 57 (2000).
2. C. Hagemann, J. L. Blank, *Cell Signal* 13: 863 (2001).
3. R. Khosravi-Far et al., *Mol Cell Biol* 16: 3923 (1996).
4. J. L. Bos, *Cancer Res* 49: 4682 (1989).
5. A. Borg et al., *Cancer Res* 50: 4332 (1990).
6. D. J. Slamon et al., *Science* 235: 177 (1987).
7. G. L. Johnson, R. Lapadat, *Science* 298: 1911 (2002).
8. B. A. Ballif, J. Blenis, *Cell Growth Differ* 12: 397 (2001).
9. J. A. Fresno Vara et al., *Cancer Treat Rev* 30: 193 (2004).
10. C. L. Yu et al., *Science* 269: 81 (1995).
11. W. Jin et al., *Br J Cancer* 89: 185 (2003).
12. C. B. Weldon et al., *Surgery* 132: 293 (2002).
13. J. S. Sebolt-Leopold, *Oncogene* 19: 6594 (2000).
14. J. S. Sebolt-Leopold et al, *Nat Med* 5: 810 (1999).
15. S. M. Sebti, A. D. Hamilton, *Pharmacol Ther* 74: 103 (1997).
16. C. R. Weinstein-Oppenheimer, W. L. Blalock, L. S. Steelman, F. Chang, J. A. McCubrey, *Pharmacol Ther* 88: 229 (2000).
17. J. M. Kyriakis el al., *Nature* 358: 417 (1992).
18. J. M. English, M. H. Cobb, *Trends Pharmacol Sci* 23: 40 (2002).
19. D. Hao, E. K. Rowinsky, *Cancer Invest* 20: 387 (2002).
20. C. Lavoie et al., *J Biol Chem* 277: 35402 (2002).
21. P. J. Stork, J. M. Schmitt, *Trends Cell Biol* 12: 258 (2002).
22. E. Di Marco et al., *Oncogene* 4: 831 (1989).
23. T. P. Fleming, T. Matsui, S. A. Aaronson, *Exp Gerontol* 27: 523 (1992).
24. M. Watanabe, A. Nobuta, J. Tanaka, M. Asaka, *Int J Cancer* 67: 264 (1996).
25. J. Graells et al., *J Invest Dermatol* 123: 1151 (2004).
26. A. S. Dhillon, W. Kolch, *Arch Biochem Biophys* 404: 3 (2002).
27. J. S. Strobl, W. F. Wonderlin, D. C. Flynn, *Gen Pharmacol* 26: 1643 (1995).
28. J. Wu et al., *Science* 262: 1065 (1993).
29. B. R. Sevetson, X. Kong, J. C. Lawrence, Jr., *Proc Natl Acad Sci USA* 90: 10305 (1993).
30. L. M. Graves et al., *Proc Natl Acad Sci USA* 90: 10300 (1993).
31. A. Budillon et al., *Br J Cancer* 81: 1134 (1999).
32. S. Maudsley et al., *J Biol Chem* 275: 9572 (2000).
33. P. Erhardt, J. Troppmair, U. R. Rapp, G. M. Cooper, *Mol Cell Biol* 15: 5524 (1995).
34. M. R. Vossler et al., *Cell* 89: 73 (1997).
35. S. Hafner et al., *Mol Cell Biol* 14: 6696 (1994).
36. J. M. Schmitt, P. J. Stork, *Mol Cell Biol* 21: 3671 (2001).
37. J. M. Schmitt, P. J. Stork, *Mol Cell* 9: 85 (2002).
38. G. Tortora, F. Ciardiello, *Ann N Y Acad Sci* 968: 139 (2002).
39. V. Grassi, S. Daniotti, M. Schiassi, M. Dottorini, C. Tantucci, *Int J Clin Pharmacol Res* 6: 93 (1986).
40. W. Biemacki, K. Prince, K. Whyte, W. MacNee, D. C. Flenley, *Am Rev Respir Dis.* 139(2): 492-7 (1989).

What is claimed is:

1. A method for suppressing tumor growth in breast cancer, central nervous system cancer, or renal cancer in an individual in need thereof comprising administering to the individual an amount of a B2AR agonist that is effective for suppressing tumor growth, wherein the B2AR agonist is ARA-211 or isoproterenol and wherein the tumor expresses B2AR, c-Raf-1, P-Erk 1/2 and Erk 1/2.

2. The method of claim 1 wherein the Erk 1/2 is inhibited from being phosphorylated.

3. A method for treating breast cancer, central nervous system cancer, or renal cancer in an individual in need thereof comprising administering to the individual an effective amount of a B2AR agonist, wherein the B2AR agonist is ARA-211 or isoproterenol and wherein the cancer expresses B2AR, c-Raf-1, P-Erk 1/2 and Erk 1/2.

4. The method of claim 3 wherein the Erk 1/2 is inhibited from being phosphorylated.

5. A method of delaying the development of breast cancer, central nervous system cancer, or renal cancer in an individual in need thereof comprising administering to the individual an amount of ARA-211 or isoproterenol and wherein the cancer expresses B2AR, c-Raf-1, P-Erk 1/2 and Erk 1/2.

* * * * *

UNITED STATES PATENT AND TRADEMARK OFFICE
CERTIFICATE OF CORRECTION

PATENT NO. : 7,713,960 B2  Page 1 of 1
APPLICATION NO. : 11/490777
DATED : May 11, 2010
INVENTOR(S) : Said M. Sebti It is certified that error appears in the above-identified patent and that said Letters Patent is hereby corrected as shown below:

Column 18:

- In claim 1, line 44, after the word 'P-Erk 1/2', please replace "and" with --and/or--.

- In claim 3, line 52, after the word 'P-Erk 1/2', please replace "and" with --and/or--.

- In claim 5, line 59, after the word 'P-Erk 1/2', please replace "and" with --and/or--.

Signed and Sealed this

Tenth Day of August, 2010

David J. Kappos
*Director of the United States Patent and Trademark Office*